(12) United States Patent
Teshima

(10) Patent No.: US 9,228,961 B2
(45) Date of Patent: Jan. 5, 2016

(54) METHOD FOR PRODUCING STRUCTURE

(71) Applicant: CANON KABUSHIKI KAISHA, Tokyo (JP)

(72) Inventor: Takayuki Teshima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 54 days.

(21) Appl. No.: 13/924,816

(22) Filed: Jun. 24, 2013

(65) Prior Publication Data
US 2013/0343524 A1    Dec. 26, 2013

(30) Foreign Application Priority Data

Jun. 26, 2012 (JP) .................................. 2012-143143

(51) Int. Cl.
*G21K 1/06* (2006.01)
*G01N 23/20* (2006.01)

(52) U.S. Cl.
CPC ............ *G01N 23/20008* (2013.01); *G21K 1/06* (2013.01); *G21K 1/062* (2013.01); *G21K 2207/005* (2013.01)

(58) Field of Classification Search
CPC ...... B60K 5/04; B60K 5/1208; B60K 5/1216; B60K 5/1241; G01T 1/24; G21K 1/06; G21K 1/062; G01N 23/207; G01N 23/20008; G01N 23/02; G01N 23/04; G02B 6/13; G02B 6/136; H01L 21/3205; H01L 21/32055; H01L 29/06; H01L 2924/00; H01L 2924/0002
USPC ............ 378/34, 35, 36, 71, 145, 147; 216/24, 216/39; 438/584, 597, 669, 734
See application file for complete search history.

(56) References Cited

U.S. PATENT DOCUMENTS

2008/0068047 A1* 3/2008 Hashimoto .................. 327/88

FOREIGN PATENT DOCUMENTS

| JP | 2004-015001 A | | 1/2004 | |
| JP | 2004-057507 A | | 2/2004 | |
| JP | 2004057507 | * | 2/2004 | ............... A61B 6/03 |
| JP | 2012-93332 A | | 5/2012 | |
| JP | 2012-093429 A | | 5/2012 | |
| WO | WO2011122506 | * | 6/2011 | ............... G21K 1/02 |

OTHER PUBLICATIONS

Takahashi et. al., Fabrication of X-rays mask with carbon membrane for diffraction gratings, Mar. 2010, Microsystem Technologies, vol. 16, No. 8-9, p. 1303-1305.*

(Continued)

*Primary Examiner* — Irakli Kiknadze
*Assistant Examiner* — Julio M Duarte-Carvajalino
(74) *Attorney, Agent, or Firm* — Canon USA Inc. IP Division

(57) ABSTRACT

A method for producing a structure includes the steps of etching a first substrate of an integrated member including, in sequence, the first substrate, an etching stop layer, and a seed layer, from a surface of the first substrate opposite the surface adjacent to the etching stop layer to form a hole or a plurality of gaps in the first substrate in such a manner that part of a surface of the etching stop layer is exposed, partially etching the etching stop layer from the surface of the etching stop layer exposed to expose part of a surface of the seed layer, and forming a metal member by plating using the seed layer as a seed to charge a metal into at least part of the hole or the gaps.

11 Claims, 8 Drawing Sheets

(56) References Cited

OTHER PUBLICATIONS

Groot et. al., The processing of eWaste. Part 1: The preparation and characterization of a metallic alloy derived from the smelting of printed circuit boards, Dec. 2009, The Journal of the Southern African Institute of Mining and Metallurgy, vol. 109, p. 697, 698.*

Madou, Fundamentals of Microfabrication: The Science of Miniaturization, Mar. 2002, second Edition, chapter 6: LIGA and Micromolding, CRC Press, p. 325, 327, 335, 337.*

Dixit et. al., Mechanical and microstructural characterization of high aspect ratio through-wafer electroplated copper interconnects, Aug. 2007, J. Micromech. Microeng. vol. 17, p. 1749-1751.*

Fisher et. al., Selective electroless nickel plating on oxygen-plasma-activated gold seed-layers for the fabrication of low contact resistance vias and microstructures, Jan. 2010, IEEE 23rd International Conference on Micro Electro Mechanical Systems (MEMS), p. 472.*

Kohl, Modern Electroplating 5th Edition, Chapter 4: Electrodeposition of Gold, Oct. 2010, Wiley, p. 115.*

Matsumoto et. al., Fabrication of diffraction grating for X-ray Talbot interferometer, Mar. 2007, Microsyst Technol., vol. 13, p. 544, 545.*

* cited by examiner

METHOD FOR PRODUCING STRUCTURE

BACKGROUND OF THE INVENTION

1. Field of the Invention

The present invention relates to a method for producing a structure.

2. Description of the Related Art

Diffraction gratings formed of structures having periodic structures have been used as spectroscopic elements for various apparatuses. In particular, structures composed of metals having high X-ray absorptivity have been used for nondestructive inspection of objects and in the medical field.

An example of the applications of structures composed of metals having high X-ray absorptivity is a shield grating in an image pick-up apparatus configured to pick-up an image using the Talbot interference of X-rays. An image pick-up method using the Talbot interference of X-rays (X-ray Talbot interferometry) is one of the imaging methods (X-ray phase imaging methods) using phase contrast of X-rays.

X-ray Talbot interferometry is briefly described. In a common image pick-up apparatus using X-ray Talbot interferometry, spatially coherent X-rays pass through a diffraction grating and a specimen which diffract X-rays to form an interference pattern. A shield grating configured to periodically shield X-rays is arranged at a position where the interference pattern is formed, thereby forming moire. The moire is detected with a detector. An image is obtained from the detection results.

A common shield grating used in Talbot interferometry has a structure in which X-ray shielding portions (hereinafter, also simply referred to as "shielding portions") and X-ray transmitting portions (hereinafter, also simply referred to as "transmitting portions") are arranged at a pitch of about 2 to about 8 μm, depending on imaging resolution required. The X-ray shielding portions are often formed of a structure which is composed of, a metal having high X-ray absorptivity, such as gold, and which has a high aspect ratio (the aspect ratio indicates the ratio of the height or depth h to the width w of a structure, i.e., h/w).

The shield grating having such a structure may be used to not only partially shield X-rays that form an interference pattern to form moire but also improve the spatial coherence of X-rays as described above. The shield grating used in this way is referred to as a "source grating". When the source grating is arranged between an X-ray source and a diffraction grating, it is possible to virtually produce a state in which microfocus X-ray sources are arranged. A smaller focal point of an X-ray source (X-ray generating point) results in higher spatial coherence of X-rays generated from the X-ray source. Thus, the use of the source grating improves the spatial coherence of X-rays. Talbot interferometry performed by virtually forming the state in which the microfocus X-ray sources are arranged is referred to as "Talbot-Lau interferometry. The shield grating in this specification includes the source grating, unless otherwise specified.

As a method for producing such a shield grating, a method in which a metal is charged into a mold by plating is known.

Japanese Patent Laid-Open No. 2012-93332 discloses a method for forming a metal member by etching an etching substrate of a substrate in which an electrically conductive substrate and the etching substrate are bonded together to form a plurality of grooves and charging gold into each of the grooves by plating using the electrically conductive substrate as a seed layer.

In Japanese Patent Laid-Open No. 2012-93332, however, the electrically conductive substrate is likely to be etched, depending on an etching method of the etching substrate and the material of the electrically conductive substrate. If the electrically conductive substrate is etched, the starting position of charging of gold may vary.

SUMMARY OF THE INVENTION

The present invention provides a method for producing a structure by charging a metal into a mold using plating, in which variations in the starting position of the plating are reduced.

One disclosed aspect of the present invention provides a method for producing a structure including the steps of etching a first substrate of an integrated member including, in sequence, the first substrate, an etching stop layer, and a seed layer, from a surface of the first substrate opposite the surface adjacent to the etching stop layer to form a hole or a plurality of gaps in the first substrate in such a manner that part of a surface of the etching stop layer is exposed, partially etching the etching stop layer from the surface of the etching stop layer exposed to expose part of a surface of the seed layer, and forming a metal member by plating using the seed layer as a seed to charge a metal into at least part of the hole or the gaps.

Further features of the present invention will become apparent from the following description of exemplary embodiments with reference to the attached drawings.

DESCRIPTION OF THE EMBODIMENTS

Figure 1A:
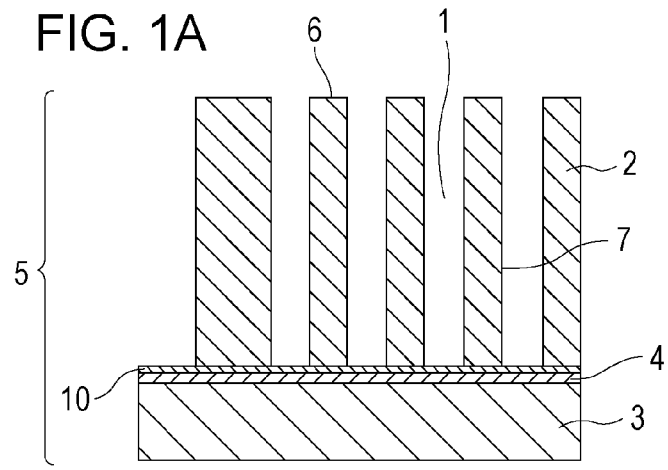
FIGS. 1A to 1C are process drawings illustrating a first embodiment of the present invention.

Embodiments of the present invention will be described in detail below.

First Embodiment

In this embodiment, the case where a structure produced in this embodiment used as an X-ray shield grating used in X-ray Talbot interferometry is used will be described. However, the structure produced in this embodiment may also be used for other applications. The structure produced in this embodiment is a shield grating in which X-ray shielding portions (hereinafter, also simply referred to as "shielding portions") and X-ray transmitting portions (hereinafter, also simply referred to as "transmitting portions") are arranged. In the case where the structure produced in this embodiment is used as a shield grating for the X-ray Talbot interferometry, the X-ray-screening portion may screen 80% or more of incident X-rays. In the case where a void is formed in a metal body included in the screening portion, when the structure is used as an X-ray shield grating, the amount of X-rays absorbed is reduced, thereby reducing the contrast in the amount of X-rays transmitted between the X-ray shielding portions and the X-ray transmitting portions. In the X-ray Talbot interferometry, a reduction in the contrast of the amount of X-rays transmitted through a shield grating used commonly reduces the resolution and the contrast of an image to be formed.

A method for producing a shield grating according to this embodiment includes:

(1) a step of etching a first substrate of an integrated member including, in sequence, the first substrate, an etching stop layer, and a seed layer, in which the first substrate is etched from a surface of the first substrate opposite the surface adjacent to the etching stop layer until part of a surface of the etching stop layer is exposed, thereby forming a hole or a plurality of gaps in the first substrate;

(2) a step of partially etching the etching stop layer from the surface of the etching stop layer exposed on the side of the first substrate, in which the etching is performed until part of a surface of the seed layer adjacent to the first substrate (on the side of the etching stop layer) is exposed;

(3) a step of forming a first insulating film on the top face of the first substrate and the side wall of the hole or side walls of the plural gaps; and (4) a step of forming a metal member by plating the surface of the seed layer adjacent to the first substrate using the seed layer as a seed to charge a metal into at least part of the hole or the gaps.

In step (1), the use of the integrated member including the first substrate and the seed layer enables electroplating to be performed without forming a new seed layer. In the case where a seed layer is formed on a substrate having a hole (groove) or gaps, for example, vapor deposition may be employed. However, in the case where a seed layer is vapor-deposited, a substance to be vapor-deposited is less likely to enter the substrate perpendicularly to a substrate surface as a distance from the center of the substrate is increased, causing difficulty in vapor-depositing the seed layer. Thus, in the case where the seed layer is vapor-deposited, it is difficult to increase the area of the substrate on which the seed layer is vapor-deposited. In contrast, in this embodiment, the first substrate and the seed layer are bonded in step (1); hence, there is no need to vapor-deposit the seed layer. Furthermore, the integrated member includes, in sequence, the first substrate, the etching stop layer, and the seed layer; hence, when the first substrate is etched, it is possible to prevent the etching from reaching the seed layer. This results in a reduction in the variation of the thickness of the metal member to be formed and a reduction in variations in the X-ray shielding ratio of the shielding portions of the shield grating.

The foregoing steps will be described in more detail below with reference to FIGS. 1A to 1C.

Steps (1) to (4) described above correspond to first to fourth steps. For illustrative purposes, the integrated member including, in sequence, the first substrate, the etching stop layer, and the seed layer is also referred to as a "substrate in which the first substrate and the seed layer are bonded with the etching stop layer provided therebetween" or simply as a "bonded substrate". In this case, the bonded substrate includes not only a member in which the etching stop layer and the seed layer are laminated on the first substrate but also the first substrate including the etching stop layer and the seed layer formed by, for example, the vapor deposition of metal layers.

First Step

In the first step according to this embodiment, a substrate in which the first substrate and the seed layer are bonded with the etching stop layer provided therebetween is formed, and then the first substrate is etched to form a hole or a plurality of gaps in the first substrate (FIG. 1A). The first step will be described with reference to FIGS. 2A to 2D.

A bonded substrate 5 in which a first substrate 2 and a seed layer 4 are bonded with an etching stop layer 10 provided therebetween is formed. In this embodiment, a second substrate 3 is bonded to a surface of the seed layer 4 opposite the surface adjacent to the first substrate to reinforce the bonded substrate 5.

The first substrate 2 may have low X-ray absorptivity and may be patterned by etching. For example, a silicon substrate that may be processed by a semiconductor process may be used.

The seed layer 4 may be electrically conductive and may be composed of a metal. A material that is commonly used for a seed layer may be used for the seed layer according to this embodiment. Gold or a gold alloy may be used. The seed layer may not be a single layer. For example, a gold layer and a nickel layer may be laminated together to form a seed layer.

The etching stop layer 10 may suffice to inhibit the etching of the seed layer 4 during the etching of the first substrate 2. The material and the thickness of the etching stop layer 10 may be appropriately selected, depending on an etching method of the first substrate 2. The etching stop layer 10 may have etching resistance to the etching method of the first substrate 2. The etching rate of the etching stop layer may be 1 or less with respect to 100 of the etching rate of silicon.

For example, in the case where the first substrate 2 is etched by reactive-ion etching (RIE) using the Bosch process, which is known as an etching method appropriate for deep etching of silicon, a chromium layer may be used as the etching stop layer 10. In this case, the chromium layer may have a thickness of 5 nm or more and about 1 μm or less. The RIE using the Bosch process refers to RIE in which etching with $SF_6$ gas and sidewall protective film deposition with $C_4F_8$ gas are alternately performed.

The second substrate 3 may have low X-ray absorptivity and may be composed of, for example, silicon, quartz, or polyimide.

Figure 2A:
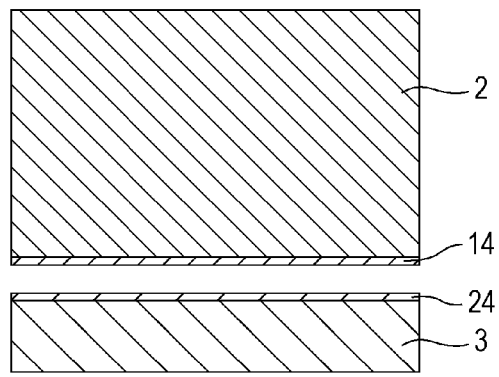
FIGS. 2A to 2D are process drawings illustrating a first step of the first embodiment of the present invention.
Figure 2C:
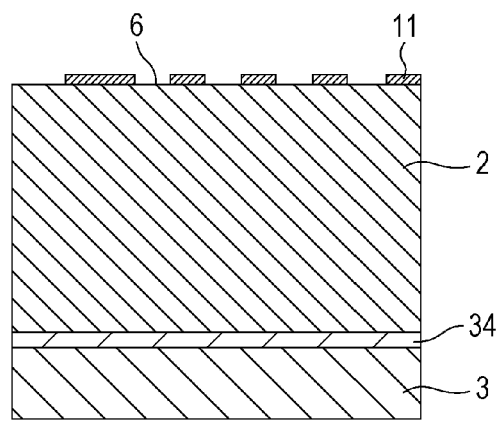
Figure 2B:
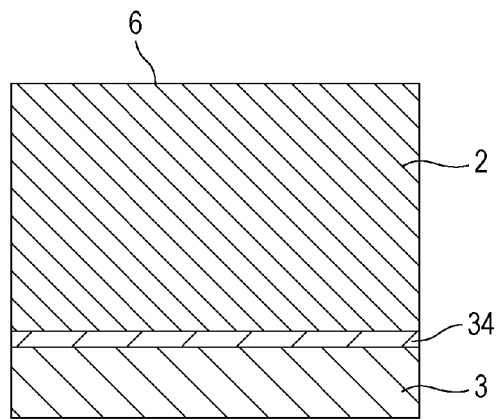

FIGS. 2A and 2B illustrate an example of a method for forming the bonded substrate 5 in which the first substrate and the seed layer are bonded with the etching stop layer provided therebetween, in which a silicon substrate is used as the first substrate 2, and metals are used as materials for the seed layer and the etching stop layer.

As illustrated in FIG. 2A, the first substrate 2 and the second substrate 3 are prepared. A metal layer 14 is formed on the first substrate. A metal layer 24 is formed on the second substrate. Each of the metal layers 14 and 24 may be a single layer or multilayer.

The fact that each of the substrates is prepared indicates that each of the substrates may be formed or may be available by purchase or the like.

Copper, nickel, iron, chromium, titanium, tin, or gold may be used as a metal for the bonding surface between the first substrate and the metal layer 14. The same is true for the bonding surface between the second substrate and the metal layer 24.

As illustrated in FIG. 2B, the first substrate 2 and the second substrate 3 are bonded via the metal layers 14 and 24 provided on the respective bonding surfaces of the substrates. Thereby, the metal layer 14 provided on the first substrate and the metal layer 24 provided on the second substrate are bonded together to form a metal layer 34.

The metal layer 34 includes the etching stop layer 10 and the seed layer 4. At this point, the metal layers 14 and 24 are formed on the first substrate 2 and the second substrate, respectively, in such a manner that the etching stop layer is formed between the seed layer and the first substrate. The first substrate 2 may not be directly bonded to the etching stop layer 10. The first substrate and the etching stop layer may be bonded with another layer provided therebetween. In the case where a layer composed of a material having low X-ray transmittance is bonded, the transmitting portions also have low X-ray transmittance. Thus, a material having low X-ray transmittance may be bonded.

In this case, the bonding surfaces of the metal layer 14 on the first substrate and the metal layer 24 on the second substrate may be composed of gold. The reason for this is that when the bonding surfaces of the metal layer 14 on the first substrate and the metal layer 24 on the second substrate are composed of gold, it is possible to industrially bond the metal layers to each other at normal temperature, as typified by gold bumps. While the example of a method for forming the substrate in which the first substrate and the seed layer are bonded with the etching stop layer provided therebetween has been described, a method for forming the bonded substrate is not limited to the foregoing method.

The first substrate is etched to form a plurality of gaps 1 in the first substrate, thereby forming a pattern in the first substrate. The etching is performed until the etching reaches the etching stop layer and the etching stop layer is partially exposed on the side of the first substrate.

Figure 5A:
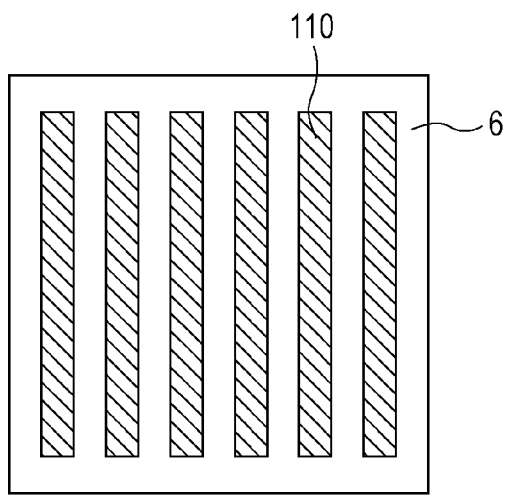
FIGS. 5A to 5D are top views illustrating exemplary patterns of a first substrate according to the first embodiment of the present invention.
Figure 5B:
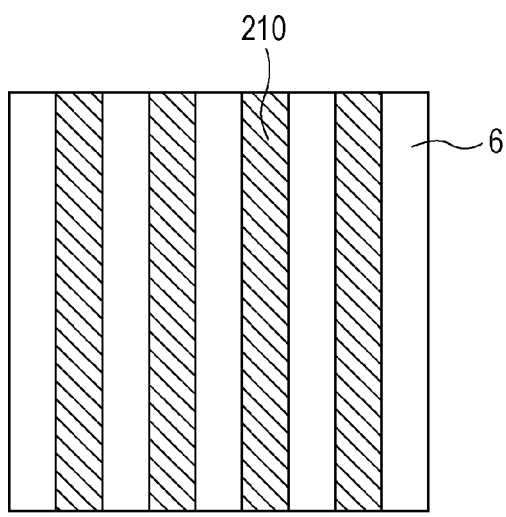
Figure 5C:
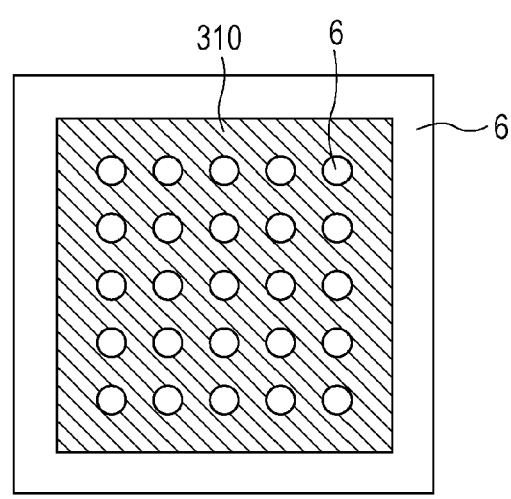
Figure 5D:
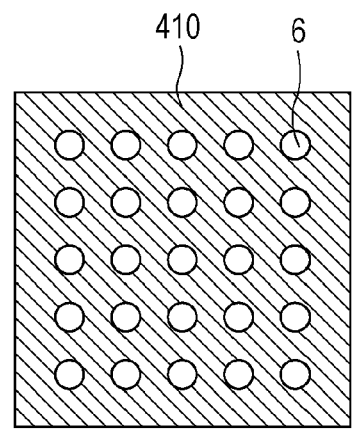

The shape and the size of the pattern formed in the first substrate are determined by a periodic pattern of a structure to be formed. In the case where the structure is used as an X-ray shield grating configured to produce moire by the X-ray Talbot interferometry, a line- or dot-like pattern having a pitch of ten-odd micrometers to several micrometers is commonly used. FIGS. 5A to 5D illustrate examples of the pattern formed in the first substrate 2. FIGS. 5A to 5D are top views and illustrate a top face 6 of the first substrate. In FIG. 5A, a pattern is formed in the first substrate by the formation of line-like gaps 110 in the first substrate. In FIG. 5B, line-like gaps 210 are formed between portions of the first substrate by the arrangement of the line-like portions, spaced one another, of the first substrate. A pattern is formed by the arrangement of the portions of the first substrate and the gaps 210. In this case, in a third step described below, when a metal is charged into the gaps 210, the metal is required not to flow out in the vertical direction in FIG. 5B. For example, a frame which covers at least the vertical direction of the gaps 210 and which is formed of a material different from the first substrate may be formed. As described above, the gaps are defined as being formed in the first substrate even if upper and lower ends of each of the gaps 210 are not sandwiched between the portions of the first substrate. FIG. 5C illustrates an example of the first substrate in which a hole 310 is formed in the first substrate in such a manner that dot-like portions of the first substrate are arranged so as to be spaced from one another. As just described, the hole may be formed instead of the plural gaps. While this specification basically describes the case where the gaps are formed, the same effect is provided for the case where the hole is formed. FIG. 5D illustrates a pattern without the frame surrounding the hole 310 illustrated in FIG. 5C. Also in this case, as with FIG. 5B, it is necessary to take measures to prevent a metal that is charged into a hole 410 in the third step from flowing out. As just described, the hole 410 is defined as being formed in the first substrate even if a region of the hole 410 is only partially sandwiched between the portions of the first substrate.

Here, in the patterns formed in or between the first substrates, portions of the first substrates function as transmitting portions of a shield grating, and the gaps between the first substrates function as shielding portions of the shield grating.

An example of a method for etching the first substrate to form such a pattern will be described below.

As illustrated in FIG. 2C, a mask layer 11 is formed on the top face 6 of the first substrate 2 (a face of the first substrate 2 opposite the face adjacent to the etching stop layer). The top face 6 of the first substrate 2 is partially exposed from the mask layer 11 to form a mask pattern. A pattern to be formed in the first substrate is determined by the mask pattern formed here. In the case where a $SiO_2$ film is formed on the top face 6 of the first substrate 2 in advance, the $SiO_2$ film may be used as the mask layer 11. In the case where the $SiO_2$ film is used as the mask layer 11, the $SiO_2$ film can be left on the top face 6 also after the formation of the pattern in the first substrate and can function as an (second) insulating film in the subsequent step. For example, description will be made on the case where the $SiO_2$ film is used as the mask layer 11 and where a mask patter is formed with a photoresist. The $SiO_2$ film is formed on the top face 6. A photoresist is applied on the $SiO_2$ film. The photoresist is exposed to form a pattern. The $SiO_2$ film exposed from the pattern of the photoresist is etched to expose the top face of the first substrate. This results in the first substrate in which the mask layer including the $SiO_2$ film and the photoresist is arranged and the top face is partially exposed from the mask layer. The etching of the $SiO_2$ film may be performed by, for example, a dry etching method. Among dry etching methods, a dry etching method with $CHF_3$ plasma may be employed. After the etching of the $SiO_2$ film, the photoresist may be removed.

Figure 2D:
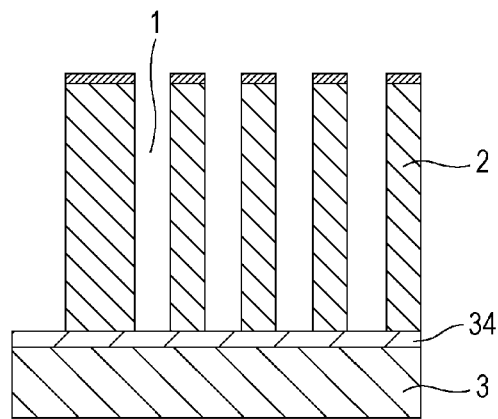

As illustrated in FIG. 2D, the first substrate 2 is etched with the mask layer 11 as a mask to expose the metal layer 34, thereby forming a hole or gaps (110, 210, 310, or 410 in FIGS. 5A to 5D) in the first substrate. A metal is charged into the hole or the gaps in the third step described below to form a metal member 9. In the case where a structure produced in this embodiment is used as a shield grating to form moire by X-ray Talbot interferometry, the metal member 9 functions as an X-ray shielding portion. A greater depth of the gaps results in an increase in the X-ray shielding ratio. Furthermore, a narrower pitch of the arrangement of the metal member 9 results in improvement in the resolution of an image to be formed by imaging. Thus, a higher aspect ratio of the gaps results in improvement in the resolution of the image to be formed by imaging. In the case where the structure is used as a shield grating for use in X-ray Talbot interferometry, the aspect ratio of the gaps may be 10 or more and 150 or less. The aspect ratio of the gaps refers to the aspect ratio of a gap having the smallest width among the gaps. For example, in the case where the gaps are formed so as to form the pattern illustrated in FIG. 5A or 5B, the aspect ratio is defined as the ratio of the width (in the transverse direction in the figure) of each gap 110 or 210 sandwiched by the portions of the first substrate to the depth (in the direction perpendicular to the paper plane in the figure) of the gap. Furthermore, for example, in the case where a hole is formed so as to form the pattern illustrated in FIG. 5C or 5D, is defined as the ratio of the width of a portion between the dot-like portions of the first substrate to the depth of the hole 310 or 410.

As a method for etching the first substrate 2, a wet etching method with a solution or a dry etching method, for example, ion sputtering or reactive gas plasma, may be employed.

Among dry etching methods using reactive gas plasma, reactive ion etching (RIE) may be employed for the formation of gaps having a high aspect ratio. In particular, RIE using the Bosch process may be employed for the formation of gaps having a higher aspect ratio.

As illustrated in FIGS. 2A to 2D, in the case of using the substrate in which the first substrate 2 and the metal layer 34 are directly bonded together, in etching using plasma, if the first substrate 2 is charged by the impact of plasma, the electrical charge is efficiently removed with the metal layer 34. Thus, even if the first substrate 2 has a pillar structure as illustrated in FIG. 5C, the sticking of adjacent pillars is inhibited, thereby reducing the nonuniformity of the pitch of the pattern formed in the first substrate. Furthermore, the use of a conductive substrate as the second substrate 3 enhances the effect of removing the electrical charge. In the case of employing RIE by the Bosch process, the sidewall protective film may be removed after the RIE. Examples of a removal method include oxygen plasma asking and washing with a hydrofluoroether (HFE) solution.

By performing the foregoing steps, it is possible to prepare the substrate 5 in which the first substrate 2 composed of silicon and provided with the hole or the plural gaps is bonded to the second substrate 3 with the metal layer 34 provided therebetween. The metal layer includes at least the etching stop layer 10 and the seed layer 4.

The step of etching the first substrate of the substrate, in which the first substrate is bonded to the seed layer with the etching stop layer provided therebetween, to form a pattern may be performed by a method other than the method that has been described with reference to FIGS. 2A to 2D. For example, the first substrate may be bonded to the seed layer with the etching stop layer provided therebetween. After the first substrate is etched, the second substrate may be bonded to the first substrate. Alternatively, the second substrate may not be provided, depending on the strength of the first substrate, the etching stop layer, and the seed layer. However, in the case of forming the pattern in which portions of the first substrate are partially spaced as illustrated in any of FIGS. 5B to 5D, after the first substrate is bonded to the second substrate with the metal layer provided therebetween, the pattern may be formed in the first substrate, as the method illustrated in FIGS. 2A to 2D. Also in the case where the first substrate that is bonded to the seed layer with the etching stop layer provided therebetween is etched to expose the etching stop layer and where the second substrate is bonded thereto, the pattern in which portions of the first substrate are partially spaced may be formed. However, in the case of this method, if each of the etching stop layer and the seed layer has a small thickness, it is difficult to maintain the pattern. If each of the etching stop layer and the seed layer has a large thickness, the X-ray shielding ratio of the transmitting portions can be increased.

The substrate in which the first substrate is bonded to the seed layer with the etching stop layer provided therebetween as illustrated in FIG. 2B may be obtained by purchase, and the first substrate may be etched to form the hole or the plural gaps.

Second Step

The etching stop layer may be present between the first substrate and the seed layer during the etching of the first substrate. Thus, after the first substrate is etched, the etching stop layer 10 is partially removed to expose the seed layer 4. With respect to a method for removing the etching stop layer, a method for selectively removing the etching stop layer may be selected in view of materials of the etching stop layer and the seed layer. For example, in the case where the etching stop layer is composed of chromium, the etching stop layer may be removed by etching with an aqueous chromium etching solution. The etching stop layer may be removed before plating. For example, the order of the second step and the third step described below may be changed. At least part of the seed layer may be exposed. Thus, the exposed portion of the etching stop layer other than the portion sandwiched between the first substrate and the seed layer may be partially or completely removed.

Third Step

Figure 1B:
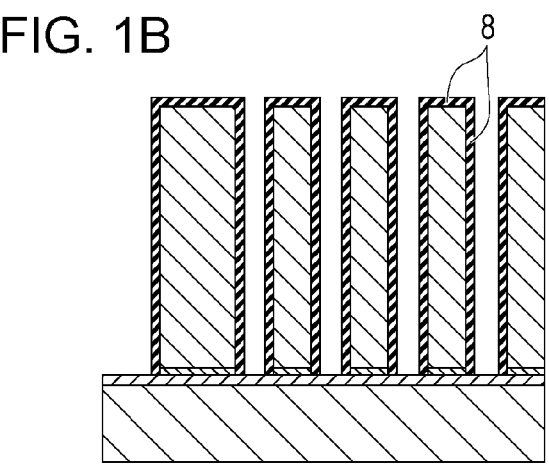

In the third step, as illustrated in FIG. 1B, a first insulating film 8 is formed on the top face 6 and side walls 7 of the gaps 1 in the first substrate of the bonded substrate 5 produced in the first step. The first insulating film may have a thickness of 0.01 µm or more and 5 µm or less.

The formation of the first insulating film 8 on the top face 6 and the side walls 7 of the gaps 1 in the first substrate inhibits the formation of a void due to the precipitation of a metal from the side walls and the top face.

Depending on the material of the first substrate and the metal charged by plating, migration can occur at the interface between the metal and the first substrate because of direct contact between the metal and the first substrate. The migration refers to a phenomenon in which a metal component is moved in a non-metal medium by the effect of an electric field. The occurrence of the migration reduces the amount of X-rays transmitted through the transmitting portions at the interfaces between the transmitting portions and the shielding portions, thereby leading to a reduction in the contrast in the amount of X-rays transmitted between the transmitting portions and the shielding portions (hereinafter, also referred to as an "X-ray transmission contrast").

In this embodiment, the first insulating film is formed on the side walls 7 of the gaps 1 before the metal is charged. Thus, the first insulating film functions as a migration-inhibiting layer, thereby inhibiting the occurrence of the migration.

Depending on the resistance of the first substrate, current during electroplating, the metal charged, and the pattern in the first substrate, the formation of a void is negligible without forming the first insulating film, in some cases.

In some cases, migration occurs negligibly. In those cases, the first insulating film may not be formed, and the third step may be omitted.

A method for forming the first insulating film is not particularly limited. Examples of the method that may be employed include chemical vapor deposition (CVD), thermal oxidation, electron beam evaporation, and vacuum sputtering. In the case where the first substrate is subjected to RIE using the Bosch process in the first step, CVD or thermal oxidation may be employed. It is known that when the first substrate is etched by RIE using the Bosch process, a continuous stepped structure, which is referred to as scallops, is formed on the side walls 7 of the gaps 1 in the first substrate. In the case where the insulating film is formed by CVD or thermal oxidation, the insulating film can be formed also in recesses or shadowed portions in the stepped structure when viewed from the top face 6.

CVD used in this specification indicates that a source gas containing a component for a target insulating film is fed onto a heated substrate in a reduced pressure atmosphere and a chemical reaction occurs on a substrate surface or in a vapor phase to form an insulating film. In CVD, the insulating film can be formed on the substrate at a substrate temperature of 300° C. or lower. Thus, the first insulating film can be deposited at a temperature equal to or lower than the melting point of the seed layer 4. When the substrate is heated to a temperature equal to or higher than the melting point of the seed layer 4, the pitch of the pattern formed in the first substrate can vary.

In the case where a silicon substrate is used as the first substrate, in this specification, the formation of an insulating film composed of an organopolysiloxane by vaporizing a precursor of the organopolysiloxane and subjecting the precursor to polycondensation in a vapor phase is also included in the formation of an insulating film by CVD.

A natural oxide film is present on the top face 6 and the side walls 7 of the gaps in the first substrate 2. When the vaporized precursor of the organopolysiloxane enters the gaps, silanol groups (Si—OH) on a surface of the natural oxide film and the precursor of the organopolysiloxane are bonded together by polycondensation. Then the organopolysiloxane bonded to the silanol groups (Si—OH) on the surface of the natural oxide film is subjected to polycondensation with the precursor of the organopolysiloxane to form an insulating film in which the chemical bonds in the organopolysiloxane are repeated.

In this embodiment, a silane coupling agent may be used as the precursor of the organopolysiloxane. The use of the silane coupling agent facilitates the formation of an insulating film composed of a dialkylpolysiloxane or a monoalkylpolysiloxane in a vapor phase.

In this embodiment, examples of the silane coupling agent that may be used to form the dialkylpolysiloxane include dimethyldimethoxysilane, dimethyldiethoxysilane, dimethyldichlorosilane, dimethyldibromosilane, dimethyldimethoxysilane, dimethyldiethoxysilane, dimethyldichlorosilane, and diethyldibromosilane.

Examples of the silane coupling agent that may be used to form a monoalkylpolysiloxane include trimethoxymethylsilane, triethoxymethylsilane, trichloromethylsilane, tribromomethylsilane, trimethoxyethylsilane, triethoxyethylsilane, trichloroethylsilane, tribromoethylsilane, trimethoxypropylsilane, triethoxypropylsilane, trichloropropylsilane, tribromopropylsilane, trimethoxybutylsilane, triethoxybutylsilane, trichlorobutylsilane, tribromobutylsilane, decyltrichlorosilane, hexyltrimethoxysilane, cyclohexyltrichlorosilane, n-dodecyltriethoxysilane, n-octyltrichlorosilane, n-octyltriethoxysilane, octadecyltriethoxysilane, and pentyltriethoxysilane.

In the case where a silicon substrate is used as the first substrate, the first insulating film may be formed by thermal oxidation. Thermal oxidation of silicon results in the formation of the first insulating film 8 also in recesses in steps on the side walls 7 or shadowed portions of the gaps 1 when viewed from the top face 6. However, in the case where silicon is thermally oxidized, the silicon substrate is heated to about 1000° C. The etching stop layer and the seed layer can be heated to about their melting points to cause the pitch of the gaps 1 to vary, depending on materials of the etching stop layer and the seed layer. In particular, in the case where silicon portions, each being in the form of a pillar, of the first substrate are arranged to form a pattern as illustrated in FIG. 5C or 5D, heating the seed layer to a temperature close to the melting point can cause the pillars to fall down, so that the pattern can vary. Thus, the materials of the etching stop layer and the seed layer may be selected in view of the temperature of the thermal oxidation. Alternatively, the first insulating film may be formed by CVD.

Fourth Step

Figure 1C:
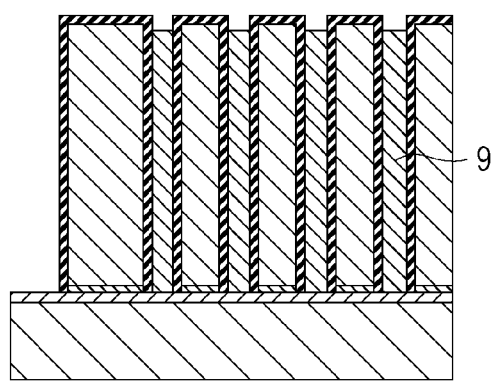

As illustrated in FIG. 1C, a surface of the seed layer adjacent to the first substrate is plated using the seed layer 4 as a seed to charge a metal into at least some of the gaps in the first substrate, thereby forming the metal member 9. In the case where the structure produced in this embodiment is used as an X-ray shield grating, the metal charged in this step is selected from metals each having high X-ray absorptivity. Examples of metals each having high X-ray absorptivity include gold, tungsten, and alloys thereof.

To perform plating using the seed layer 4 as a seed, it is necessary to expose part of the seed layer 4. Thus, in the case where the etching stop layer 10 and the first insulating film 8 are formed on the seed layer 4, they are removed to expose part of the seed layer. Part of the seed layer may indicate the entire portion of the seed layer other than a portion of the seed layer where the etching stop layer and the first substrate are formed on the seed layer (a portion where the hole or the plural gaps are formed).

In this embodiment, the first insulating film formed on the seed layer or the etching stop layer is selectively removed. Plating is performed while the first insulating film formed on the side walls 7 of the gaps and the top face 6 of the first substrate is left.

To selectively remove the first insulating film on the seed layer 4, a highly anisotropic etching method (anisotropic etching) may be employed. Examples of the anisotropic etching method include ion sputtering and a reactive gas plasma etching method. In the case where the anisotropic etching method is employed, the first insulating film on the seed layer 4 is preferentially removed with respect to the first insulating film formed on the side walls 7 of the gaps because of the anisotropy of etching. However, the first insulating film formed on the top face 6 of the first substrate is removed in the same way as the insulating film on the seed layer. Thus, an insulating film in addition to the first insulating film is formed in advance on the top face 6 of the first substrate in such a manner that the thickness of the insulating film on the top face is larger than the thickness of the first insulating film on the seed layer. For example, as illustrated in FIGS. 3A to 3F, a second insulating film is formed as a mask layer used when the first substrate is etched in the first step. After the first insulating film is formed on the second insulating film, the first insulating film on the seed layer 4 is removed.

In this way, even if the first insulating film on the top face is removed by performing the removal of the first insulating film until the seed layer is exposed, at least part of the second insulating film formed on the top face is left. Furthermore, after the first insulating film is formed, a third insulating film may be selectively formed on the first insulating film by oblique deposition and then the first insulating film on the seed layer 4 may be removed. In this case, when the first insulating film on the seed layer is removed in order to expose the seed layer, the third insulating film formed by the oblique deposition is removed from the top face, and then the first insulating film is removed. It is thus possible to expose the seed layer while at least part of the first insulating film is left.

As described above, in the case where the total thickness of the films on the top face 6 of the first substrate is larger than the thickness of the first insulating film on the seed layer and where the insulating film on the seed layer is selectively removed, the total thickness of the insulating films on the top face is preferably 0.2 µm or more and more preferably 0.4 µm or more larger than the thickness of the insulating film on the seed layer.

In the case where the etching stop layer is formed below the first insulating film, the etching stop layer is removed by a method for selectively removing the etching stop layer in view of the materials of the etching stop layer and the seed layer as described in the first step.

When the seed layer 4 is connected to the cathode of an external power source and energized, plating is performed using the seed layer 4 as a seed to charge a metal into the gaps, forming the metal member 9. Thereby, a structure in which the metal member 9 is formed in the first substrate 2 is formed. In the case where a conductive substrate is used as the second substrate 3, plating may be performed by connecting the second substrate 3 to the cathode of the external power source and energizing the second substrate 3. When the second substrate is connected to the cathode and energized, an energization point configured to be connected to the cathode of the external power source may not be arranged in a surface of the first substrate 2. Thus, the pattern may be formed in a larger region of the surface of the first substrate 2 by an area needed for the arrangement of the energization point. This results in an increase in the area that functions as a grid of the X-ray shield grating.

The insulating film is formed on the top face 6 of the first substrate 2 and the side walls 7 of the gaps. Thus, a metal is selectively grown by plating on the seed layer 4. For example, even if an alkaline, non-cyan gold plating solution is used, it is possible to inhibit the precipitation of gold from the top face 6 of the first substrate 2 and the side walls 7 of the gaps. In particular, the continuous stepped structure on the side walls of the gaps formed by RIE using the Bosch process is liable to act as a reaction active site. Thus, the use of the gold plating solution is liable to cause precipitation of gold on the side walls. In this embodiment, the first insulating film is formed also on the silicon surface having the continuous stepped structure, thus, inhibiting the precipitation of gold.

The metal may not be charged into the whole space of the gaps. For example, plating may be finished when each of the gaps is filled halfway with the metal. In the case where the structure is used as an X-ray shield grating, the depth to which the metal is charged may be determined, depending on the energy of X-rays shielded and a target shielding ratio.

As illustrated in FIG. 1C, the structure produced in this embodiment includes the metal member 9 and the bonded substrate 5 in which the first substrate and the seed layer are bonded with the etching stop layer provided therebetween. The first substrate includes the patterned gaps. The metal member is arranged in each of the gaps. In the case where the structure is used as an X-ray shield grating, the metal member functions as a shielding portion. Thus, the pattern of the gaps formed in the first substrate is formed so as to correspond to the pattern of the shielding portions of the X-ray shield grating to be produced.

Second Embodiment

Figure 6A:
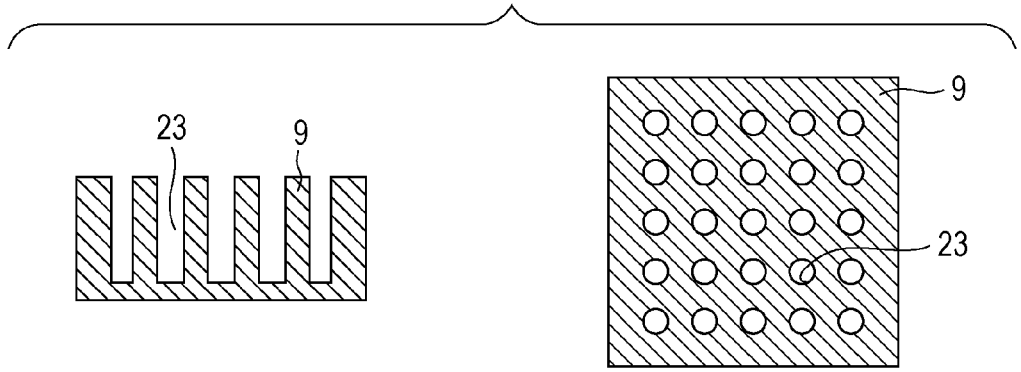
FIGS. 6A to 6C are process drawings illustrating a second embodiment of the present invention.
Figure 6B:
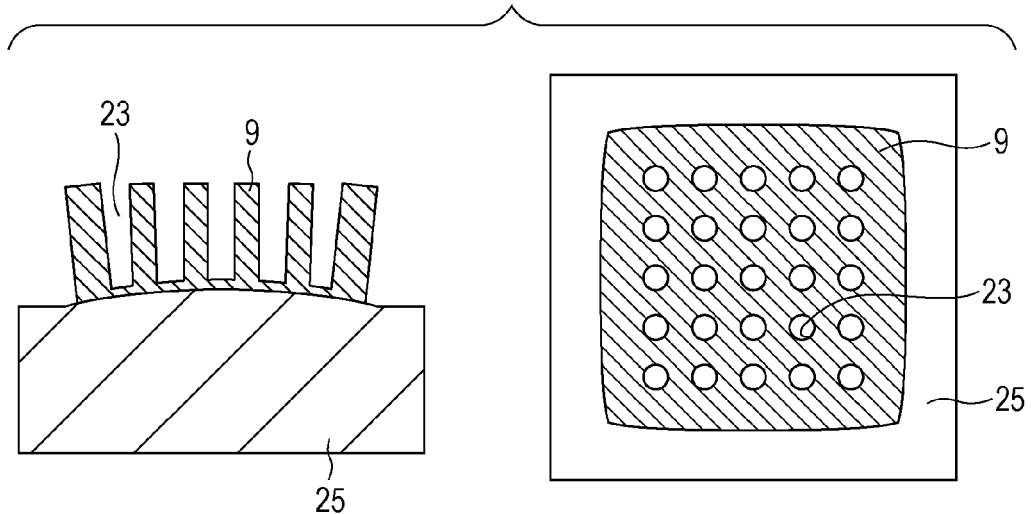

In a second embodiment, a method for producing a structure serving as a shield grating used in the Talbot interferometry by further processing the structure produced in the first embodiment will be described with reference to FIGS. 6A to 6C.

This embodiment includes the steps of forming a structure in the same way as in the first embodiment (the first to fourth steps in the first embodiment); a step of taking out the metal member 9 from the structure produced in the steps in the same way as in the first embodiment; and a step of applying a resin to the resulting metal member 9 and solidifying the resin to form a resin layer 22.

In this embodiment, for illustrative purposes, the method for producing a structure is described using the first substrate having the pattern as illustrated in FIG. 5C. However, another pattern may be formed.

The step of taking out the metal member 9 (FIGS. 6A and 6B) is performed by etching the first substrate 2 and the second substrate 3. With respect to an etching method, any of wet etching methods and dry etching methods may be employed as long as the etching method is a method such that the charged metal member 9 is less likely to be etched. For example, in the case where the first substrate and the second substrate are composed of silicon and where the metal member is composed of gold, an aqueous solution of hydrofluoric acid and nitric acid may be used in the wet etching method. In the case where the first insulating film is composed of $SiO_2$ or SiN, it is possible to etch the first insulating film with the aqueous solution of hydrofluoric acid and nitric acid. Furthermore, an aqueous solution of an inorganic alkali, for example, potassium hydroxide or sodium hydroxide, or an alkaline aqueous solution of an organic compound, for example, tetramethylammonium hydroxide, hydrazine, or ethylenediamine may also be used. An example of the dry etching method is etching using XeF as a reactive gas. XeF is a gas capable of selectively etching silicon. In this embodiment, the metal member may be taken out from the first substrate and the second substrate. In the case where the material of the seed layer is the same as that of the metal member, the seed layer is integrated with the metal member to cause difficulty in removing the seed layer from the metal member, in some cases. The seed layer may not be removed from metal member. Parts of the first substrate and the second substrate, the insulating film, and so forth may be left in addition to the seed layer. The taken metal member 9 has a structure in which high-aspect-ratio holes 23 are arranged in portions where the first substrate has been present (FIG. 6B).

Figure 6C:
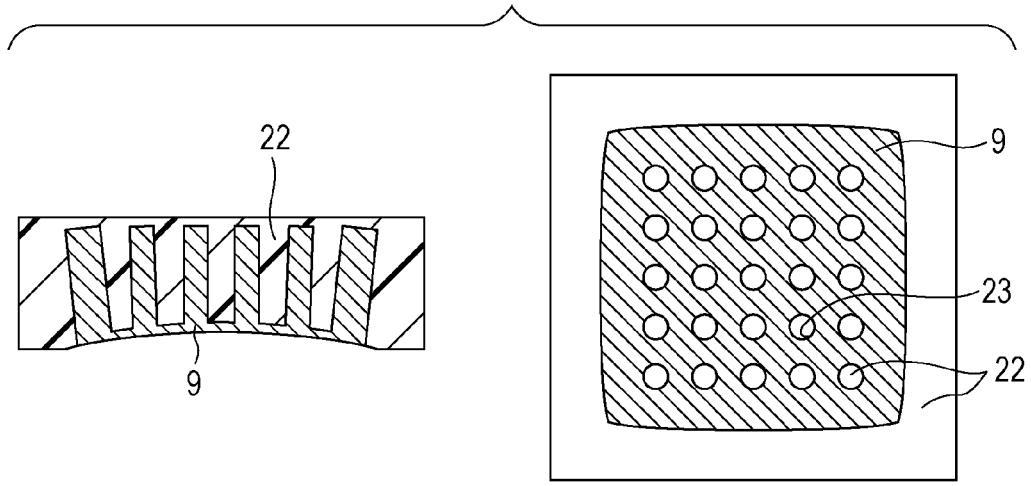

Next, a resin is applied on a surface of the taken metal member and in the holes 23 formed in the metal member and solidified to form the resin layer 22 (FIG. 6C). In this embodiment, the resin is not necessarily charged into all the holes 23. A void may be formed in the resin in the holes. Solidification used in this embodiment indicates that a flowable resin is cured by, for example, ultraviolet rays, heat, or the use of a catalyst. Examples of the resin that may be used include ultraviolet curable resins, thermosetting resins, and two-component curable resins. The formation of the resin layer 22 on the metal member 9 improves the strength and the handleability of the removed metal member 9. In general, resins have lower X-ray absorptivity than silicon substrates. Thus, in the case where the first substrate and the second substrate are composed of silicon, when the structure produced in this embodiment is used as a shield grating for use in the X-ray Talbot interferometry, the structure produced in this embodiment has a high transmission contrast, compared with the case where the structure produced in the first embodiment is used as a shield grating.

Figure 7A:
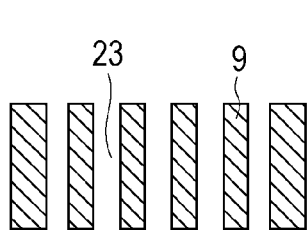
FIGS. 7A to 7C are process drawings illustrating a modification of the second embodiment of the present invention.
Figure 7A:
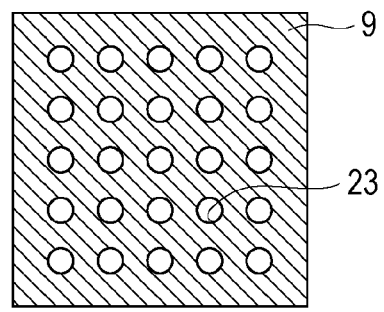
Figure 7B:
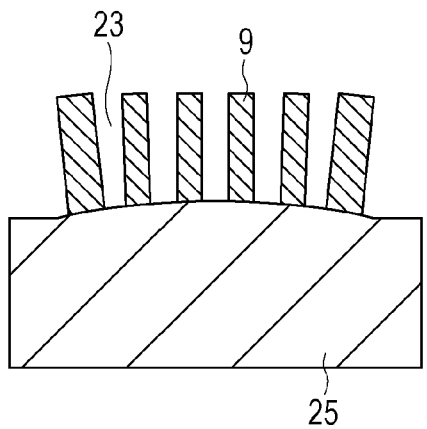
Figure 7B:
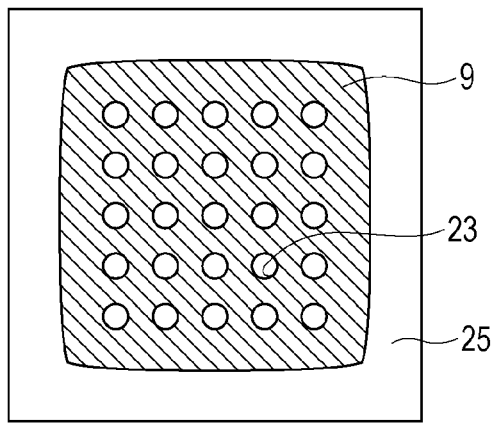
Figure 7C:
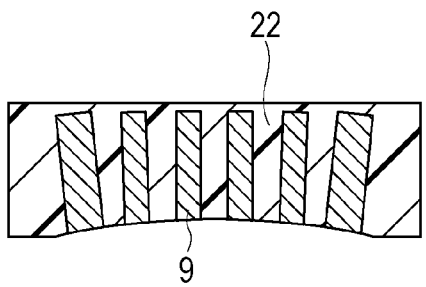
Figure 7C:
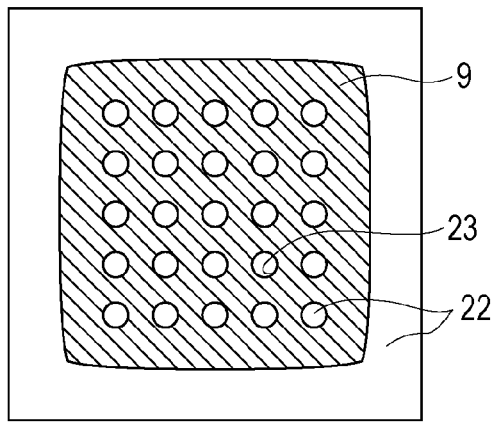

As illustrated in FIGS. 7A to 7C, when the metal member 9 is taken out (FIG. 7A) and then a step of forming a resin layer is performed while the metal member 9 is deformed (FIG. 7B), a state in which the metal member is deformed can be maintained with the resin layer (FIG. 7C). To form the resin layer with the metal member deformed, after the application of the metal member 9 with the resin, the metal member 9 may be deformed and then the resin may be solidified. Alternatively, the resin may be applied with the metal member 9 deformed and then solidified. For example, in the case where the Talbot interferometry with divergent X-rays is performed, if a planar shield grating is used, vignetting occurs, depending on the X-ray incident angle. To prevent this, a round shield grating or spherically round shield grating may be used. In this embodiment, by forming the resin layer while the metal member removed from the silicon substrate is curved in round form or spherically round form, the X-ray vignetting can be reduced.

When the resin layer is formed with the metal member deformed in round form, the depth directions of the plural holes 23 formed in the metal member reflect the round form. When the resin layer is formed with the metal member deformed in spherically round form, the depth directions of the plural holes 23 formed in the metal member can be set so as to converge to a point on the extended lines of the plural holes. Here, the round form indicates a form obtained by cutting a cylinder in the depth direction. The spherically round form indicates a continuous spherically curved surface.

As a method for deforming the metal member, for example, a method for deforming the metal member by bringing the metal member into direct or indirect contact with a mold may be employed. In the case where the metal member is deformed with the mold, a surface of the metal member brought into contact with the mold may be flat. If the surface of the metal member brought into contact with the mold is not flat, there is a risk that the metal member is not deformed as designed because of projections and recesses of the surface, so that the depth directions of the holes in the metal member are not set as designed. In this embodiment, when the first substrate is etched, the etching is stopped, so that the seed layer is not affected by the etching. Thus, in the case where the metal member is integrated with the seed layer, the bottom surface of the seed layer (a surface of the seed layer opposite the surface on which the metal member lies) is flat. In the case where the seed layer is not left on the metal member, the starting position of the plating lies on the flat seed layer, so that the bottom surface of the metal member (a surface on the side of the seed layer) is flat. Thus, when the metal member is deformed with the mold, the depth directions of the holes in the metal member are easily set as designed.

According to this embodiment, the structure as illustrated in FIG. 6C is produced, the structure including the metal member which has the plural holes 23 each having an aspect ratio of 20 or more and which is composed of gold or a gold alloy; and the resin layer 22 arranged on a surface of the metal member and at least part of the holes 23. In the case where the resin layer is formed with the metal member deformed, as illustrated in FIG. 7C, the structure reflecting the deformation is produced. For example, in the case where the resin layer is formed with the metal member deformed in round form or spherically round form, the depth direction of the holes 23 formed in the metal member also reflect the round form or spherically round form.

In this embodiment, while the holes 23 formed in the metal member are through holes, the holes 23 may not pass through the metal member 9. For example, in the case where the metal is charged by electroplating, when the height position of the top face of the metal exceeds the height position of the top face of the first substrate, the holes are not through holes. This embodiment may also be applied to such a structure.

The structure produced in this embodiment varies depending on whether the seed layer is integrally with the metal member taken out from the first substrate when the metal member is taken out from the first substrate. In the case where the seed layer is also taken out, a structure including the seed layer, the metal member formed on the seed layer, and the resin layer formed on the surface of the metal member is produced. In this case, the seed layer is formed so as to be in contact with a surface of the metal member. However, the surface on which the seed layer is formed is parallel to the direction in which the holes formed in the metal member are arranged. The metal member has the holes. The resin layer is formed in at least part of the holes. The resin layer is capable of reinforcing the metal member and maintaining the deformed state of the metal member.

In the case where the seed layer is separated from the metal member, a structure including the metal member and the resin layer formed on the surface of the metal member is produced. The metal member has holes. The resin layer is formed in at least part of the holes.

These embodiments will be described below in more detail by specific examples.

Example 1

First substrate: silicon substrate, pattern of first substrate: one dimensional, 8-μm pitch, aspect ratio of gap: 30, mask layer: $SiO_2$ film, first insulating film: silicon oxide film formed by CVD, second substrate: silicon substrate, gold plating with current energized from energization point In this example, an example according to the first embodiment is described with reference to FIGS. 3A to 3F.

Figure 3A:
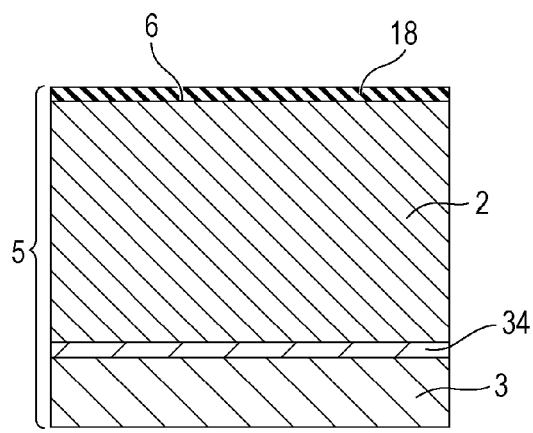
FIGS. 3A to 3F are process drawings illustrating Example 1 of the present invention.
Figure 3D:
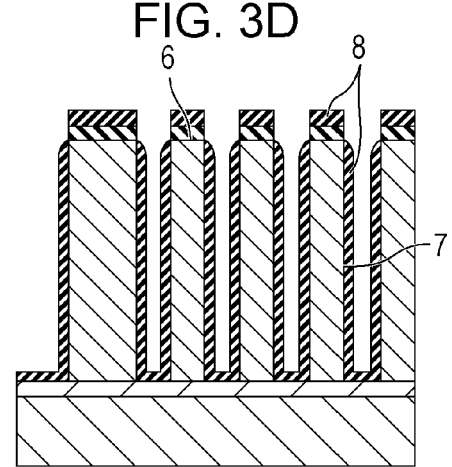
Figure 3B:
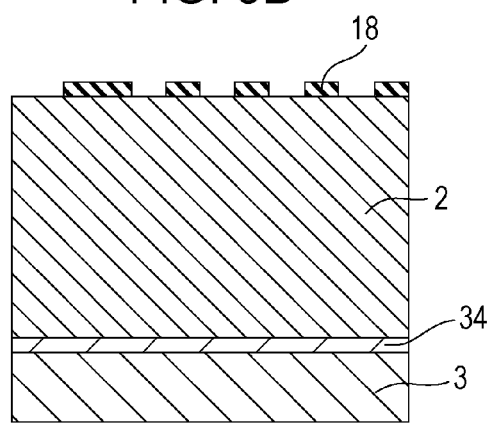
Figure 3E:
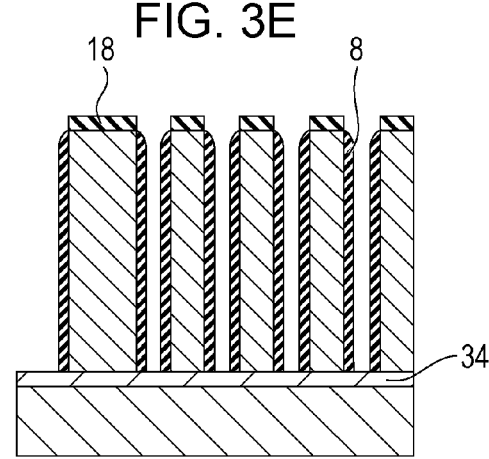
Figure 3C:
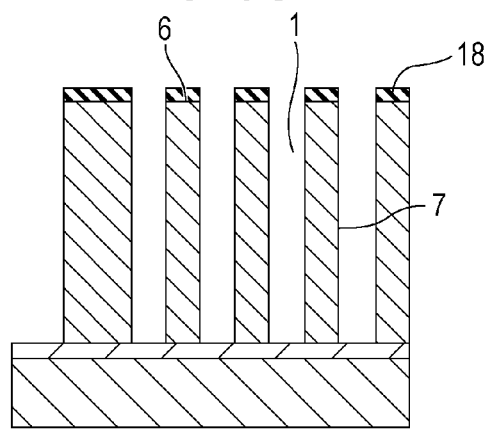

FIGS. 3A to 3C correspond to the first step in the foregoing embodiment.

FIG. 3A illustrates the substrate 5 in which the first substrate and the seed layer used in this example are bonded with the etching stop layer provided therebetween. The bonded substrate 5 has a structure in which the first substrate 2 composed of silicon and the seed layer 4 are bonded with the etching stop layer 10 provided therebetween and in which the second substrate 3 composed of silicon is bonded to the first substrate with the seed layer and the etching stop layer provided therebetween. In this example, as the first substrate 2, a silicon wafer having a diameter of 200 mm and a thickness of 200 μm is used. A thermally grown oxide film ($SiO_2$ film) having a thickness of 1.5 μm is formed as a second insulating film 18 on only one surface of the first substrate. A 10-nm-thick chromium film and a 300-nm-thick gold film are deposited, in that order, with an electron-beam vapor deposition apparatus on a surface of the substrate 5 opposite the surface on which the second insulating film is formed. The surface on which the thermally grown oxide film is formed is defined as the top face of the first substrate. As the second substrate, a silicon wafer having a diameter of 200 mm and a thickness of 200 μm is used. A 10-nm-thick chromium film and a 300-nm-thick gold film are deposited with the electron-beam vapor deposition apparatus on a surface of the second substrate. The surfaces of the first and second substrates on which the metal films are formed are bonded together using a bonding apparatus to form the bonded substrate 5. In this example, the etching stop layer is the 10-nm-thick chromium layer formed on the first substrate, and the seed layer is a 600-nm-thick gold layer. In this example, a layer corresponding to the metal layer 34 used in the description of the first step in the first embodiment is formed of the 10-nm-thick chromium layer, the 600-nm-thick gold layer, and the 10-nm-thick chromium layer.

A positive resist is applied onto the second insulating film 18. Patterning is performed in a region having a size of 130 mm×130 mm by semiconductor photolithography. The resulting pattern is a stripe-shaped pattern in which lines each having a length of 130 mm and a width of 4 μm are arranged at a pitch of 8 μm. As a result, the second insulating film 18 is exposed in stripe form. Here, a pattern serving as an energization point for plating is formed in addition to the pattern formed in the region having a size of 130 mm×130 mm. A pattern having a size of 5 mm×5 mm may be formed at a point about 10 mm distant from the periphery of the bonded substrate toward the center.

Subsequently, the second insulating film 18 is etched by reactive etching with $CHF_3$ to partially expose a surface of the first substrate composed of silicon. Then the resist is removed with N,N-dimethylformamide (FIG. 3B). In this example, the patterned second insulating film 18 is used as an etching mask in the subsequent step. Deep etching of silicon of the first substrate is performed by RIE using the Bosch process. When the deep etching is performed to a depth of 200 µm, the chromium layer serving as the etching stop layer 10 is exposed (FIG. 3C). At this point, an about 0.4-µm-thick portion of the second insulating film 18 used as the etching mask is left. Cleaning is performed by oxygen plasma asking. The exposed etching stop layer is etched with an aqueous chromium etching solution to expose the seed layer composed of gold. The etching of the etching stop layer corresponds to the second step in the first embodiment.

Next, a step corresponding to the third step in the first embodiment is performed. The first insulating film 8 is formed on the side walls 7 of the gaps of the first substrate and the top face 6 by CVD. In this example, a $SiO_2$ film is used as the first insulating film formed by CVD. A 0.1-µm-thick $SiO_2$ film is deposited with a plasma-enhanced CVD apparatus using $SiH_4$ and $N_2O$ gases at a substrate temperature of 280° C. Thereby, the first insulating film 8 having a thickness of 0.1 µm is formed on surfaces of the side walls 7, the top face 6, and the seed layer. Here, the insulating films, including the second insulating film used as the etching mask, having a thickness of about 0.5 µm are formed on the top face 6 (FIG. 3D).

The first insulating film 8 on the seed layer is partially removed, thereby resulting in a structure in which the insulating film is arranged on the top face 6 and the side walls 7 (FIG. 3E).

A dry etching method using $CHF_3$ plasma is employed for the partial removal of the first insulating film on the seed layer. This etching exhibits high anisotropy and proceeds in the direction substantially perpendicular to the substrate. In this case, the total thickness of the insulating films (the first insulating film and the second insulating film) on the top face 6 is sufficiently larger than that of the first insulating film on the seed layer. Thus, when the first insulating film on the seed layer is removed, the insulating film formed on the top face 6 and the side walls 7 is left.

Next, electroplating is performed using the exposed seed layer as a seed to charge a metal into the gaps, thereby forming a metal member. In this example, gold is used as the metal charged. The cathode of an external power source is connected to the energization point formed in the upstream step, and then electroplating is performed with a non-cyan gold plating solution (MICROFAB Au1101, available from Electroplating Engineers of Japan Ltd.) as a plating solution at a solution temperature of 60° C.

Figure 3F:
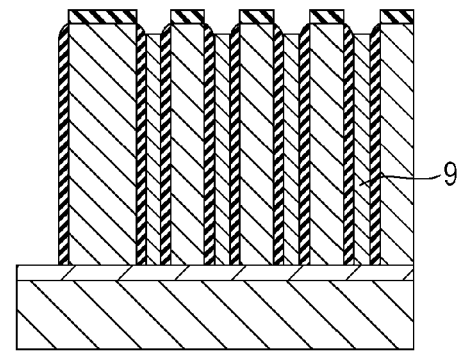

The bonded substrate is immersed in the plating solution and energized at a current density of 0.2 A/dm$^2$ for 28 hours. Thereby, gold plating using the seed layer as a seed is performed to form an about 120-µm-thick metal member 9 composed of gold (FIG. 3F). Then rinsing is performed with water, followed by drying in an oven at 100° C. Observation of a cross section with a scanning electron microscope (SEM) reveals that the metal member is dense and that substantially no void is present. Evaluations with an X-ray microscope demonstrate that a high-contrast, stripe-shaped lattice image is obtained and that the structure usable as an X-ray shield grating is produced. XRD analysis of silicon on the side walls 7 reveals that the migration of gold to silicon is not observed.

Example 2

First substrate: silicon substrate, pattern of first substrate: one dimensional, 8-µm pitch, aspect ratio of gap: 30, mask layer: photoresist, first insulating film: silicon oxide film formed by CVD, second substrate: silicon substrate In this example, an example, different from Example 1, according to the first embodiment is described with reference to FIGS. 4A to 4E.

Figure 4A:
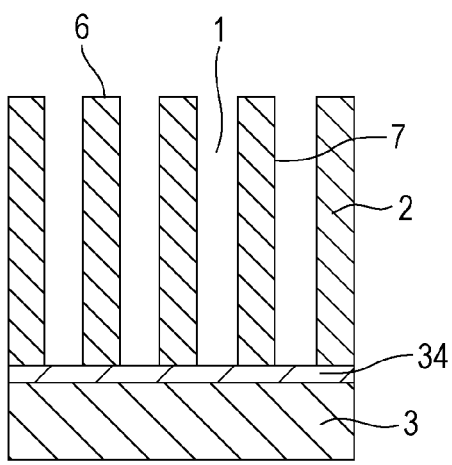
FIGS. 4A to 4E are process drawings illustrating Example 2 of the present invention.

In this example, a process for forming the substrate 5 in which the patterned first substrate and the second substrate are bonded with the seed layer provided therebetween is similar to the process according to Example 1 up to the step illustrated in FIG. 3C, so redundant description is not repeated. In this example, a photoresist is used as an etching mask in RIE using the Bosch process. Thus, the second insulating film is not formed on the top face of the first substrate. The photoresist is removed by rinsing with N,N-dimethylformamide after patterning (FIG. 4A). The energization point is formed in addition to the pattern in Example 1. In contrast, no energization point is formed in this example.

Next, the first insulating film 8 is formed on the side walls 7 and the top face 6 by CVD. In this example, a silicon nitride film is used as the first insulating film formed by CVD. The silicon nitride film having a thickness of 0.1 µm is deposited with a plasma-enhanced CVD apparatus using $SiH_4$, $NH_3$, and nitrogen gasses at a substrate temperature of 300° C. Thereby, the first insulating film having a thickness of 0.1 µm is formed on surfaces of the side walls 7, the top face 6, and the seed layer (FIG. 4B).

Next, a third insulating film 28 is formed by oblique deposition at an incident angle of 60° to the depth direction of the gaps. In this example, the third insulating film 28 is a $SiO_2$ film. The third insulating film 28 having a thickness of 0.4 µm is formed by oblique deposition on the silicon nitride film provided on the top face 6. The third insulating film 28 is not formed on the seed layer because of oblique deposition. Thereby, the total thickness of the first insulating film and the third insulating film on the top face 6 is 0.5 µm. As a result, the total thickness of the insulating films on the top face 6 is larger than that of the insulating film on the seed layer (FIG. 4C).

Figure 4D:
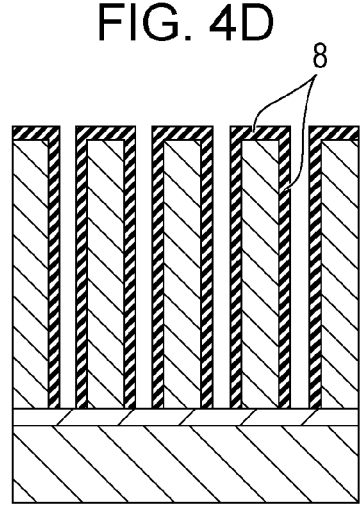
Figure 4B:
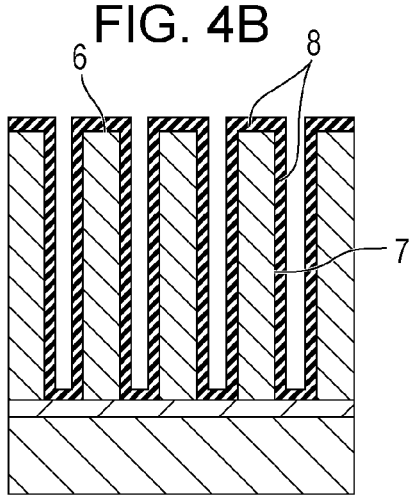

Next, the first insulating film 8 on the seed layer is partially removed, thereby resulting in a structure in which the first insulating film is arranged on the top face 6 and the side walls 7 (FIG. 4D).

As with Example 1, a dry etching method using $CHF_3$ plasma is employed for the partial removal of the insulating film on the seed layer.

Next, electroplating is performed using the exposed gold of the seed layer as a seed to charge a metal into the gaps, thereby forming a metal member. Also in this example, gold is used as the metal charged. In this example, the cathode of an external power source is connected to the second substrate. The second substrate is composed of silicon and thus a current is supplied to the seed layer through the second substrate.

A non-cyan gold plating solution (MICROFAB Au1101, available from Electroplating Engineers of Japan Ltd.) is used as a plating solution at a solution temperature of 60° C.

Figure 4E:
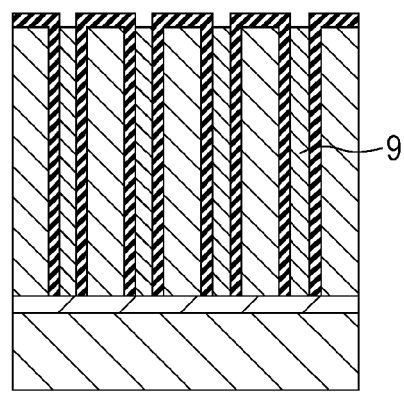
Figure 4C:
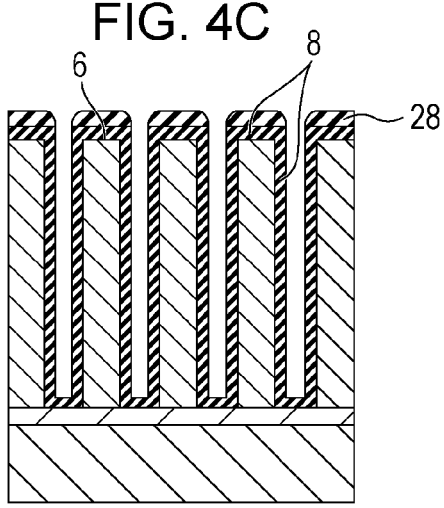

The bonded substrate is immersed in the plating solution and energized at a current density of 0.2 A/dm$^2$ for 28 hours. Thereby, gold plating using the gold seed layer as a seed is performed to form an about 120-µm-thick metal member 9 composed of gold (FIG. 4E).

Then rinsing is performed with water, followed by drying in an oven at 100° C. Observation of a cross section with a SEM reveals that the metal member is dense and that substantially no void is present. Evaluations with an X-ray microscope demonstrate that a high-contrast, stripe-shaped lattice image is obtained and that the structure usable as an X-ray shield grating is produced. XRD analysis of silicon on the side walls 7 reveals that the migration of gold to silicon is not observed.

Example 3

First substrate: silicon substrate, pattern of first substrate: two dimensional, 8-µm pitch, aspect ratio of gap: 13, mask layer: $SiO_2$, first insulating film: insulating film from silane coupling agent, second substrate: quartz In this example, an example, different from Examples 1 or 2, according to the first embodiment is described with reference to FIGS. 1A to 1C. This example differs from Example 1 in the first insulating film formed from a silane coupling agent, the second substrate composed of quartz, and the two-dimensional pattern of the gaps arranged in the first substrate. In this example, as the first substrate 2, a silicon wafer having a diameter of 100 mm and a thickness of 100 µm is used. Metal layers of a 10-nm-thick chromium layer and a 300-nm-thick gold layer are formed, in that order, with an electron-beam vapor deposition apparatus only on a surface of the first substrate. As the second substrate 3, a quartz substrate having a diameter of 100 mm and a thickness of 200 µm is used. Metal layers of a 10-nm-thick chromium layer and a 300-nm-thick gold layer are formed, in that order, with the electron-beam vapor deposition apparatus only on a surface of the second substrate 3. The gold surfaces of the metal layers of the first and second substrates are bonded together using a bonding apparatus to form the bonded substrate 5. In this example, the etching stop layer is the 10-nm-thick chromium layer formed on the first substrate, and the seed layer is a 600-nm-thick gold layer.

A positive resist is applied onto the top face 6 of the first substrate. A two-dimensional dot pattern as illustrated in FIG. 5C is formed in a region having a size of 55 mm×55 mm by semiconductor photolithography. The two-dimensional dot pattern is a pattern in which resist dots each having a diameter of 4 µm are two-dimensionally arranged at a pitch of 8 µm. Thereby, the top face of the first substrate is exposed between the resist dots each having a diameter of 4 µm. Here, a pattern serving as an energization point for plating is formed in addition to the pattern formed in the region having a size of 55 mm×55 mm. A pattern having a size of 5 mm×5 mm may be formed at a point about 10 mm distant from the periphery of the bonded substrate toward the center.

Deep etching of silicon of the first substrate is performed by RIE using the Bosch process. When the deep etching is performed to a depth of 100 µm, chromium of the etching stop layer is exposed.

Next, the photoresist is removed by oxygen plasma asking. The exposed chromium of the etching stop layer is etched with an aqueous chromium etching solution to expose the seed layer composed of gold. After rinsing with water, the bonded substrate is immersed in isopropyl alcohol. Then supercritical drying is performed using carbon dioxide. At this time, silicon of the side walls 7 and the top face 6 of the first substrate is slightly oxidized.

In this example, the third step of the embodiment is performed by a method described below. In this example, an insulating film composed of organopolysiloxane is formed as the first insulating film. A petri dish containing trimethoxymethylsilane, a petri dish containing deionized water, and the bonded substrate 5 (FIG. 1A) are placed on a hot plate at 100° C. and covered with a petri dish serving as a cover. Thereby, trimethoxymethylsilane evaporates and enters the gaps of silicon to form the first insulating film 8 composed of monomethylpolysiloxane. After 4 hours, the bonded substrate 5 is taken out and heated on the hot plate at 150° C. for 30 minutes to form a strong organopolysiloxane film on the side walls 7 and the top face 6 (FIG. 1B). Gold of the seed layer and trimethoxymethylsilane do not form a chemical bond, and thus the first insulating film is not formed on the seed layer.

Next, electroplating is performed using the exposed gold of the seed layer as a seed to charge a metal into the gaps, thereby forming a metal member. Also in this example, gold is used as the metal charged. The cathode of an external power source is connected to the energization point formed in the upstream step, and then electroplating is performed with a non-cyan gold plating solution (MICROFAB Au1101, available from Electroplating Engineers of Japan Ltd.) as a plating solution at a solution temperature of 60° C.

The bonded substrate 5 is immersed in the plating solution and energized at a current density of 0.1 A/dm² for 26 hours. Thereby, gold plating using the seed layer as a seed is performed to form an about 56-µm-thick metal member 9 composed of gold (FIG. 1C). Then rinsing is performed with water, followed by drying in an oven at 100° C. Observation of a cross section with a scanning electron microscope (SEM) reveals that the metal member is dense and that substantially no void is present. Evaluations with an X-ray microscope demonstrate that a high-contrast, stripe-shaped lattice image is obtained and that the structure usable as an X-ray shield grating is produced.

Example 4

In this example, an example of the second embodiment is described with reference to FIGS. 6A to 6C. This example describes a method in which the metal member is taken out from the structure produced in Example 1 and a resin layer is formed with the metal member deformed using a mold.

In this example, a process for forming the metal member 9 is similar to the process according to Example 1 up to the step illustrated in FIG. 3F, so redundant description is not repeated. The structure produced in Example 1 is immersed in an aqueous solution containing hydrofluoric acid and nitric acid to etch the first substrate and the second substrate, thereby taking out the metal member 9. When the aqueous solution containing hydrofluoric acid and nitric acid is used, the insulating film ($SiO_2$ film) is simultaneously etched. After the completion of the etching, the metal member 9 composed of gold is provided in the aqueous solution containing hydrofluoric acid and nitric acid. The resulting metal member is integrated with the seed layer 4 composed of gold (FIG. 6A).

Next, the resin layer is formed with the resulting metal member deformed.

An aqueous solution of a surfactant is applied to a convex mold 25 having a spherically round form with a spherical continuous curved surface and having a radius of 2 m. The metal member 9 integrated with the seed layer is placed on the mold in such a manner that a surface of the metal member 9 adjacent to the seed layer is placed on the mold. The metal member 9 adheres to the mold by the surface tension of the aqueous solution of the surfactant (FIG. 6B).

Next, an ultraviolet curable resin (TB3114, manufactured by ThreeBond Co., Ltd.) is applied to the metal member 9 on the mold 25. A quartz substrate to which a mold release agent (EGC-1720, manufactured by Sumitomo 3M Limited) is applied is placed thereon. The ultraviolet curable resin is cured by irradiation with ultraviolet rays. The separation of the metal member 9 from the quartz substrate and the mold 25 provides the metal member 9 having a spherical continuous curved surface with a radius of 2 m (FIG. 6C). The resin layer 22 maintains the shape of the metal member having the continuous curved surface. In the metal member having the curved surface maintained with the resin layer, the depth directions of the holes 23 also reflect the shape of the mold 25.

That is, the depth directions of the plural holes 23 in the structure of the metal member 9 having the spherical continuous curved surface converge to a point on the extended lines of the plural holes. The structure having such depth directions of the holes may be used as a shield grating for divergent X-rays.

Example 5

In this example, an example, different from Example 4, according to the second embodiment is described with reference to FIGS. 7A to 7C. This example differs from Example 4 in that when the metal member is taken out from the structure, the metal member is separated from the seed layer in this example.

In this example, a process for forming the metal member 9 is similar to the process according to Example 1 up to the step illustrated in FIG. 3F, so redundant description is not repeated. While the seed layer composed of elemental gold is used in Example 1, an alloy containing 90% gold and 10% tin is used in this example. Gold is charged into the gaps in the first substrate using the alloy of gold and tin as the seed layer to form the structure according to the first embodiment. The structure is immersed in an aqueous solution containing hydrofluoric acid and nitric acid to etch the first substrate and the second substrate, thereby taking out the metal member 9. When the aqueous solution containing hydrofluoric acid and nitric acid is used, the insulating film ($SiO_2$ film) and the seed layer are simultaneously etched, thereby providing the metal member 9 (FIG. 7A).

Next, a resin layer is formed with the resulting metal member deformed. This step is similar to the step described in Example 4. The metal member 9 is deformed with the convex mold 25 having a spherically round form (FIG. 7B). An ultraviolet curable resin is applied and cured to form the resin layer. The separation of the metal member 9 from the quartz substrate and the mold 25 provides the metal member 9 having a spherical continuous curved surface with a radius of 2 m (FIG. 7C). In this example, the etching stop layer protects the seed layer from etching, thereby reducing variations in the starting position of the plating. Thus, the separated metal member has a flat bottom surface and is easily deformed with the mold, compared with a metal member having uneven bottom surface.

Example 6

This example describes the case where the structure produced in Example 5 is used in an X-ray imaging apparatus using the X-ray Talbot interferometry.

The X-ray imaging apparatus according to this example includes a diffraction grating configured to diffract spatially coherent divergent X-rays to form an interference pattern, a shield grating configured to partially shield X-rays that form the interference pattern, and a detector configured to detect X-rays from the shield grating. A specimen is arranged between an X-ray source and the diffraction grating or between the diffraction grating and the shield grating. In this example, the structure produced in Example 5 is used as the shield grating. The metal member of the structure produced in Example 5 has a spherically round form. The depth directions of the holes 23 formed in the metal member converge to a point on the extended lines. The form may be used for divergent X-rays and reduces variations in contrast in the range irradiated with X-rays. The X-ray imaging apparatus may be combined with a computer serving as a computing unit configured to calculate the information of the specimen from the detection results by the detector and an X-ray source configured to irradiate the diffraction grating with X-rays, thereby providing an X-ray image pick-up system.

Comparative Example

A comparative example is described with reference to FIGS. 8A to 8C.

This comparative example differs from Example 5 in that a first substrate 102 and a seed layer 104 are bonded together without an etching stop layer.

Figure 8A:
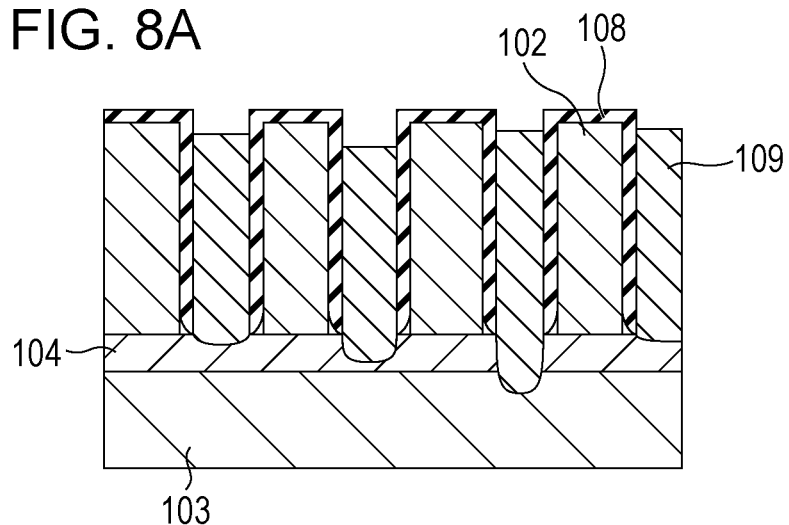
FIGS. 8A to 8C illustrate an example of a structure produced in a comparative example.
Figure 8B:
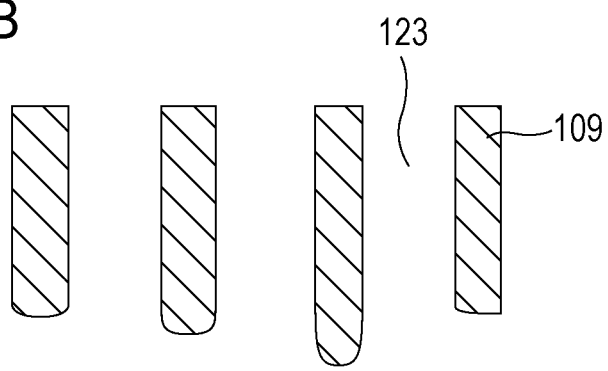
Figure 8C:
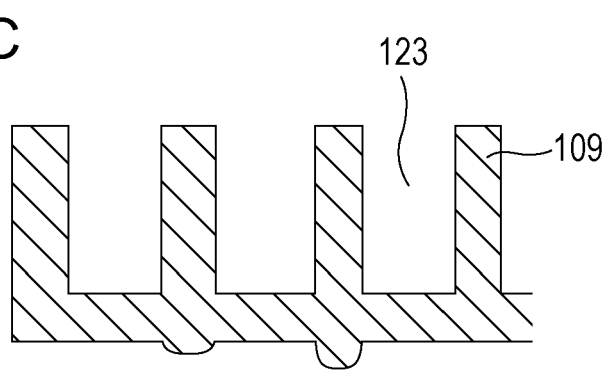

The seed layer 104 is etched to cause variations in the starting position of plating because of the absence of the etching stop layer (FIG. 8A). Thus, the X-ray shielding ratio of the shielding portions of the shield grating is likely to vary. When etching reaches a second substrate 103, the seed layer is located at not the bottom surface but the side walls of the recesses. Plating may be initiated from the side walls to cause a void in a metal member. The second substrate may be in direct contact with a metal member 109 without the insulating film 108, depending on the material of the second substrate and a method for forming an insulating film 108. In this case, the foregoing migration is likely to occur. The separated metal member has nonuniform bottom surfaces (FIG. 8B). Thus, when the metal member is deformed with a mold, directions of holes 123 formed in the metal member 109 may differ from those designed.

Even when the seed layer 104 and the metal member 109 are integrally taken out as in Example 4, in the case where the metal member 109 and the seed layer 104 are composed of different materials and have different X-ray shielding ratios, the starting position of plating is likely to vary to cause variations in X-ray shielding ratio. Furthermore, when etching reaches the second substrate, the separated metal member 109 has an uneven bottom surface (FIG. 8C). Thus, when the metal member is deformed with a mold, the directions of the holes 123 formed in the metal member may differ from those designed.

While preferred embodiments of the present invention have been described, the present invention is not limited to these embodiments. Various changes and modifications can be made without departing from the gist of the present invention. The technical elements described in the specification or illustrated in the drawings provide technical utility separately or in combination, and are not limited to the combinations stated in the claims at the time of the filing of the application. Furthermore, the techniques described in the specification or illustrated in the drawings achieve a plurality of aims simultaneously, and have technical utility in achieving any one of the plural aims.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-143143 filed Jun. 26, 2012, which is hereby incorporated by reference herein in its entirety.

What is claimed is:

1. A method for producing a structure, comprising:
    forming an integrated member by bonding a first substrate on which an etching stop layer and a first seed layer are arranged and a second substrate on which a second seed layer is arranged, in such a manner that the first seed layer and the second seed layer are in contact with each other, etching the first substrate of the integrated member,
from a surface of the first substrate opposite a surface adjacent to the etching stop layer to form a hole or a plurality of gaps in the first substrate in such a manner that part of a surface of the etching stop layer is exposed;
partially etching the etching stop layer from the surface of the etching stop layer exposed to expose part of a surface of a seed layer including the first seed layer and the second seed layer that is on a side of the first substrate; and
forming a metal member in at least part of the hole or the gaps by plating using an area of the seed layer as a seed to precipitate a metal from the area, the area being exposed by the step of partially etching the etching stop layer.

2. The method according to claim 1, further comprising:
taking out the metal member from the integrated member;
applying a resin to the metal member taken out from the integrated member; and
solidifying the resin to form a resin layer.

3. The method according to claim 1, wherein the second substrate is an electrically conductive substrate.

4. The method according to claim 1, wherein the metal member has an aspect ratio of 10 or more and 150 or less.

5. The method according to claim 1, wherein the seed layer contains gold.

6. The method according to claim 1, wherein the metal member contains gold or an alloy of gold.

7. The structure according to claim 1, wherein the seed layer is curved.

8. The method according to claim 1, wherein a surface of the first seed layer and a surface of the second seed layer are gold.

9. The method according to claim 1, wherein the first substrate is a silicon substrate and the etching stop layer contains chromium.

10. The method according to claim 1, wherein the step of forming the metal member is performed by energizing the seed layer and performing plating.

11. An X-ray imaging apparatus comprising:
a diffraction grating configured to diffract spatially coherent divergent Xrays
to form an interference pattern;
a shield grating configured to partially shield X-rays that form the interference pattern; and
a detector configured to detect X-rays from the shield grating, wherein the shield grating is a structure comprising:
an integrated member including, in sequence,
a first substrate,
an etching stop layer, and
a seed layer containing a material which differs from a material of the etching stop layer; and
a metal member provided in a hole or a plurality of gaps in the first substrate.

* * * * *